(12) United States Patent
Hibino et al.

(10) Patent No.: US 6,658,918 B2
(45) Date of Patent: Dec. 9, 2003

(54) STRUCTURE OF GAS SENSOR

(75) Inventors: Hideki Hibino, Kariya (JP); Toshimi Miyamoto, Okazaki (JP)

(73) Assignee: Denso Corporation (JP)

( * ) Notice: Subject to any disclaimer, the term of this patent is extended or adjusted under 35 U.S.C. 154(b) by 53 days.

(21) Appl. No.: 09/842,845

(22) Filed: Apr. 27, 2001

(65) Prior Publication Data
US 2001/0035045 A1 Nov. 1, 2001

(30) Foreign Application Priority Data
Apr. 28, 2000 (JP) ........................................ 2000-130429

(51) Int. Cl.$^7$ ............................ G01N 7/00; G01N 27/26
(52) U.S. Cl. ...................... 73/31.05; 73/23.31; 204/424
(58) Field of Search ................... 173/23.31, 23.32; 73/31.05; 204/424–429

(56) References Cited

U.S. PATENT DOCUMENTS

| | | | |
|---|---|---|---|
| 4,127,464 A | * 11/1978 | Ichikawa et al. | 204/410 |
| 4,214,472 A | * 7/1980 | Maxwell et al. | 73/23.31 |
| 4,611,562 A | * 9/1986 | Nakano et al. | 73/23.32 |
| 4,636,293 A | * 1/1987 | Bayha et al. | 204/428 |
| 4,730,389 A | * 3/1988 | Baudino et al. | 204/424 |
| 5,490,412 A | * 2/1996 | Duce et al. | 73/23.31 |
| 5,602,325 A | * 2/1997 | McClanahan et al. | 73/23.31 |
| 5,820,739 A | * 10/1998 | Graser et al. | 204/421 |
| 5,886,248 A | * 3/1999 | Paulus et al. | 73/23.31 |
| 5,949,023 A | * 9/1999 | Weyl | 174/77 R |
| 6,018,982 A | * 2/2000 | Friese et al. | 73/23.2 |
| 6,202,469 B1 | * 3/2001 | Nakamura et al. | 73/23.31 |
| 6,322,681 B1 | * 11/2001 | Weyl | 204/424 |
| 6,415,647 B1 | * 7/2002 | Yamada et al. | 73/31.05 |

FOREIGN PATENT DOCUMENTS

| | | |
|---|---|---|
| EP | 0918215 A2 | 5/1999 |
| JP | 2-147817 | 6/1990 |
| JP | 8-160002 | 6/1996 |
| JP | 2000-121598 | 4/2000 |

* cited by examiner

Primary Examiner—Edward Lefkowitz
Assistant Examiner—Michael Cygan
(74) Attorney, Agent, or Firm—Nixon & Vanderhye PC

(57) ABSTRACT

An improved structure of a gas sensor is provided which may be employed in an oxygen measuring device of an air-fuel ratio control system measuring an oxygen content in exhaust gasses of an internal combustion engine of automotive vehicles. The structure includes a holding mechanism disposed within an air cover installed on an end of a sensor housing to cover a base of a gas-sensing element. The holding mechanism is made of a spring member or a rigid member to retain an insulation porcelain within the air cover elastically or rigidly. The use of the holding mechanism provides for ease of installation of the insulation porcelain, results in an increase in durability of the gas sensor, and allows the overall size of the gas sensor to be decreased.

6 Claims, 18 Drawing Sheets

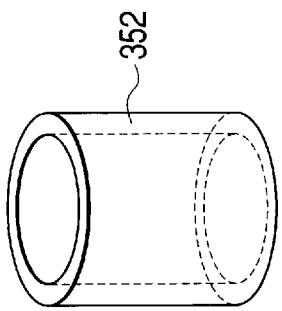
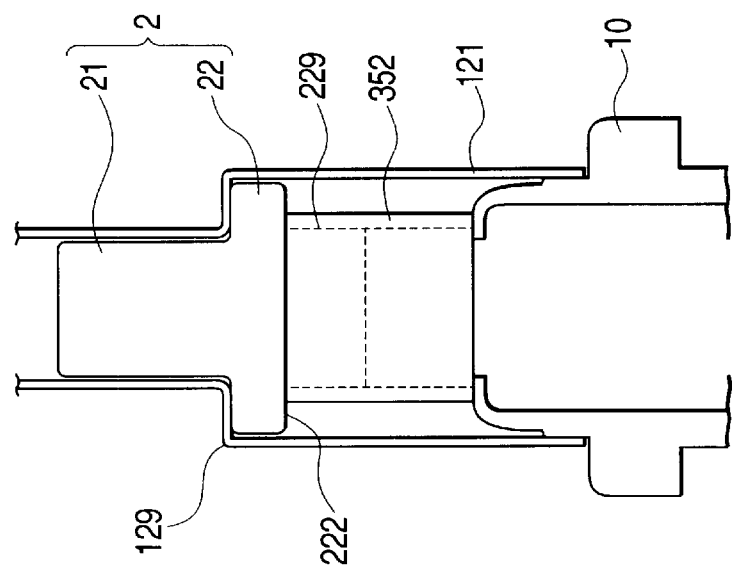
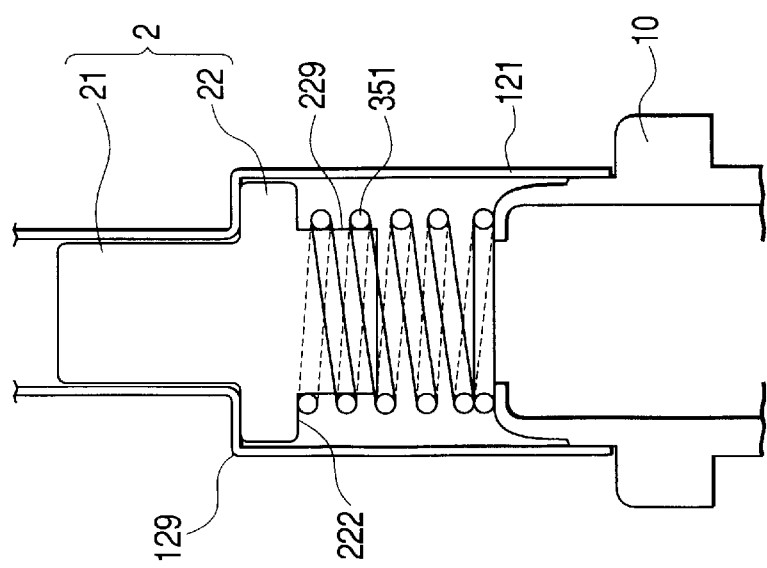

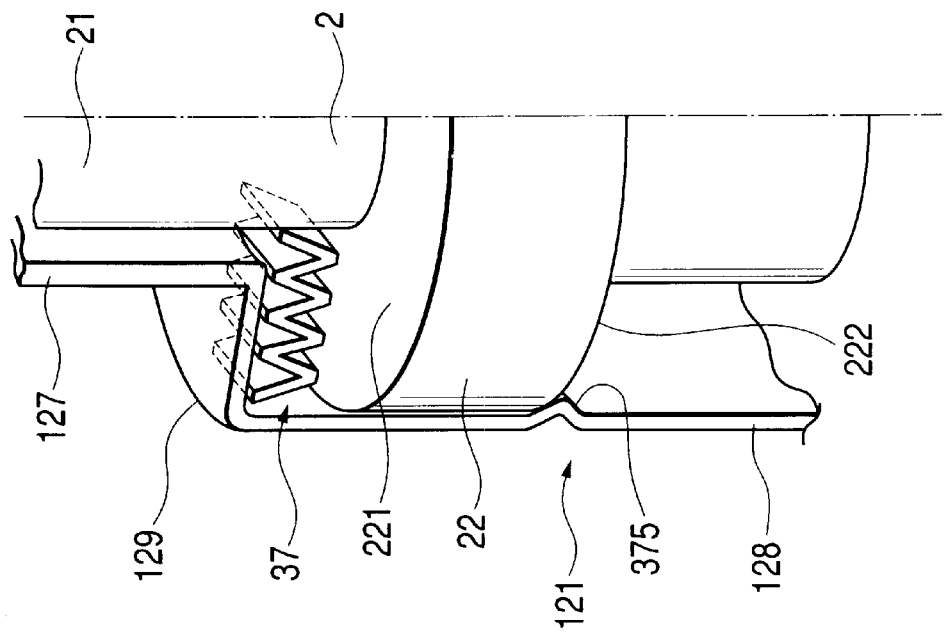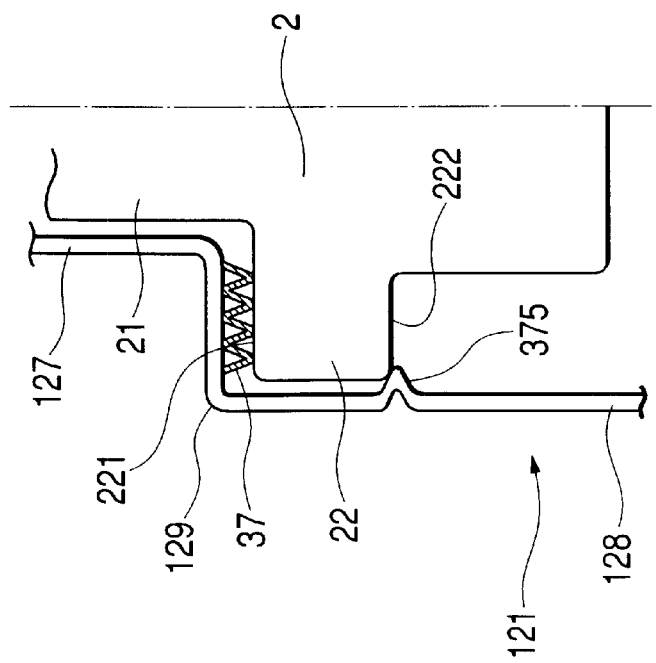

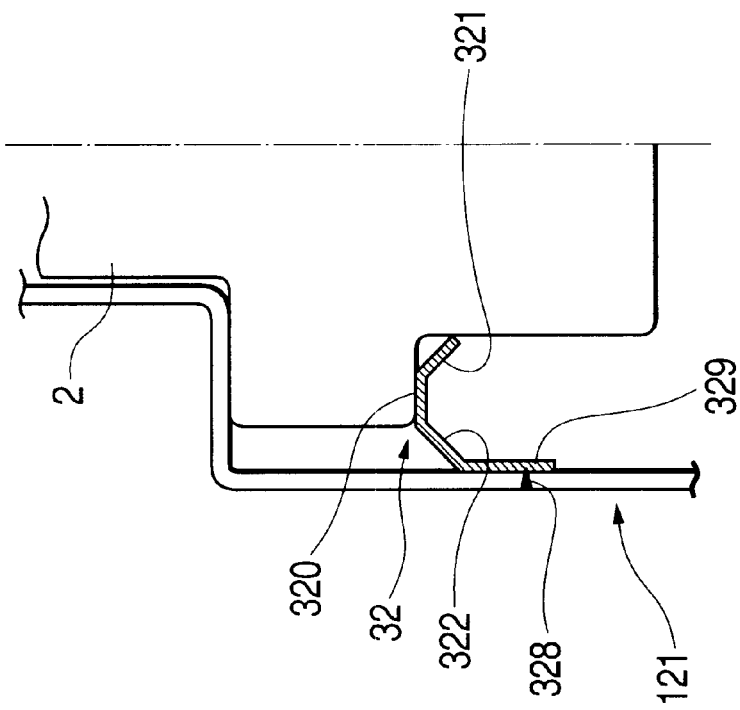
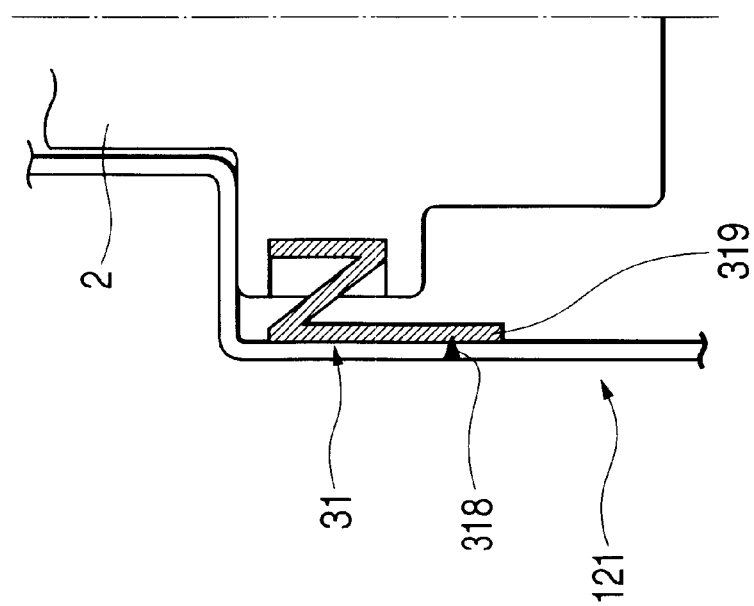

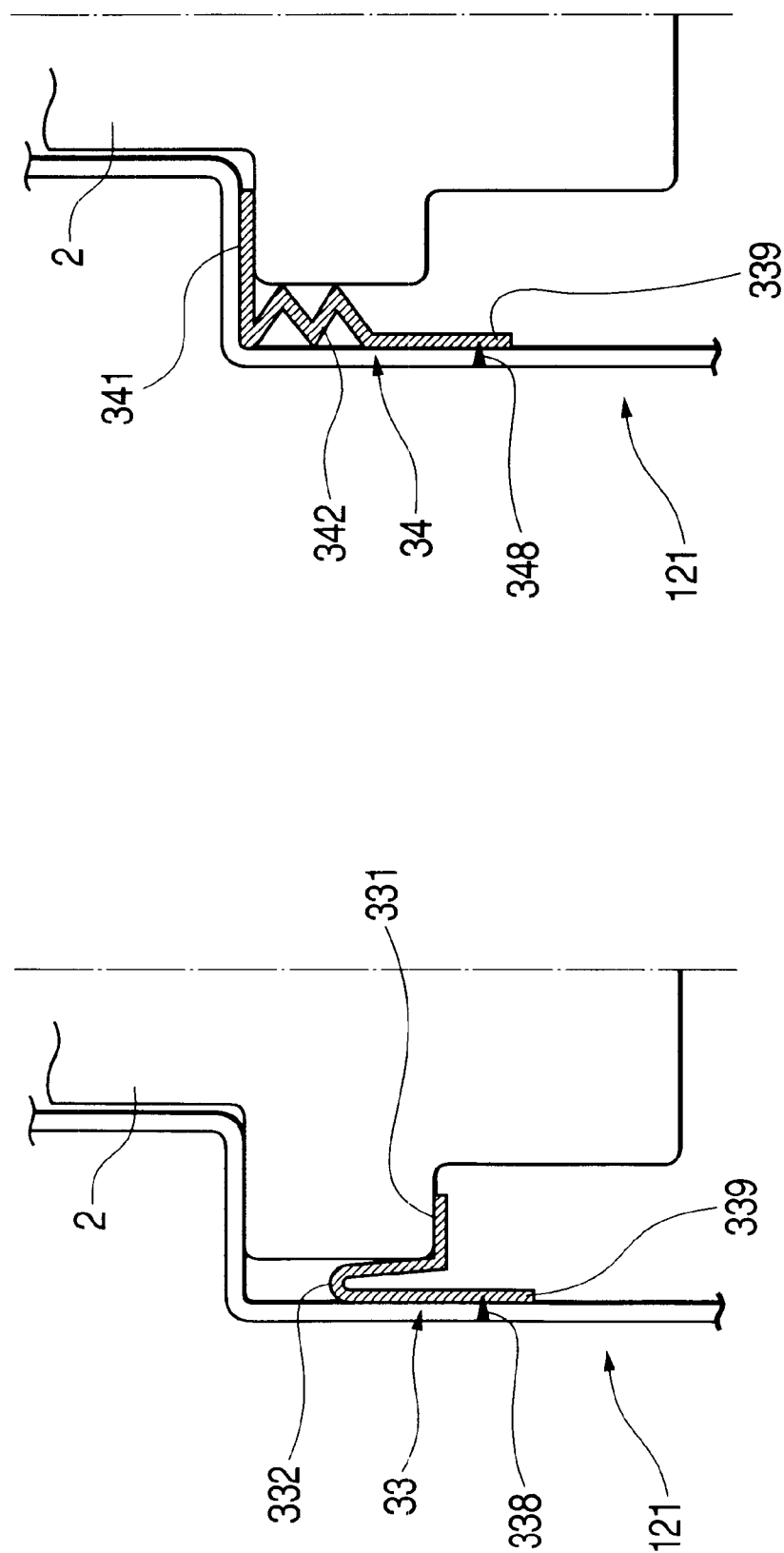

STRUCTURE OF GAS SENSOR

BACKGROUND OF THE INVENTION

1. Technical Field of the Invention

The present invention relates generally to an improvement on a gas sensor which is employed, for example, in an oxygen measuring device of an air-fuel ratio control system to measure an oxygen content in exhaust gasses of an internal combustion engine for automotive vehicles, and more particularly to an improved structure of such a gas sensor which provides for ease of installation of an insulation porcelain.

2. Background Art

It is known in the art that burning control of fuel in internal combustion engines based on an oxygen content in exhaust gasses as a parameter indicating an air-fuel ratio is effective in energy saving and emission control. As gas sensors measuring the concentration of oxygen in exhaust gasses, gas sensors equipped with a sensing element made of a solid electrolyte such as zirconia are known.

FIG. 25 shows one example of conventional gas sensors.

The gas sensor 9 consists of a sensing element 910, a housing 94, and a protective cover 92. The sensing element 910 has a portion 911 exposed to a gas to be measured and is retained within the housing 94. The protective cover 92 is installed on the housing 94 and surrounds the gas-exposed portion 911 of the sensing element 910. A packing or sealing member 918 is disposed between the housing 94 and the sensing element 910.

The sensing element 910 is of a cup-shape and has defined therein a reference gas chamber 912 leading to the atmosphere. A gas chamber 913 into which the gas to be measured is admitted is defined in the protective cover 92 around the sensing element 910. The sensing element 910 has a reference electrode exposed to the reference gas chamber 912 and a measuring electrode exposed to the gas chamber 913. The sensing element 910 also has a heater 915 disposed therein.

The sensing element 910 is electrically connected to leads 981 and 991 through coupling terminals 982 and 992 and metallic terminals 983 and 993, respectively. The metallic terminals 983 and 993 are in contact with terminals formed on the sensing element 910 leading to the reference and measuring electrodes, respectively. A lead 971 is connected to the heater 915 for supplying the power thereto.

Bases of the leads 981 and 991 connected to the coupling terminals 982 and 992 are retained within an insulation porcelain 95. The insulation porcelain 95 is held by an inner cover 931 and an outer cover 932 of an air cover assembly. Specifically, the inner cover 931 supports at an end thereof a lower portion of the insulation porcelain 95, while the outer cover 932 presses at a shoulder thereof the insulation porcelain 95 downward against the end of the inner cover 931. A disc spring 956 is disposed between the shoulder of the outer cover 932 and the insulation porcelain 95.

An air cover 933 surrounds an upper portion of the outer cover 932 through a cylindrical water-repellent filter 938 An elastic insulator 945 is fitted within an open end portion of the air cover 933 which holds the leads 971, 981, and 991 therein.

The air cover 933 and the outer cover 932 have first air vents 936 and second air vents 937, respectively, which lead to the reference gas chamber 912 through the water-repellent filter 938 for inducting the air into the reference gas chamber 912.

The elastic insulator 945, the outer cover 932 of the air cover assembly, and the air cover 933 are joined together by crimping.

The gas sensor 9 produces at the sensing element 910 an electromotive force as a function of a difference in concentration between the air in the reference gas chamber 912 and the gas in the gas chamber 913 to be measured and outputs it through the leads 981 and 991.

The above described structure of the gas sensor 9 contributes to the improvement of control ability in automotive internal combustion engines, however, it is being still required for decreasing the overall size and manufacturing costs, and improving the durability of the gas sensor 9.

SUMMARY OF THE INVENTION

It is therefore a principal object of the invention to avoid the disadvantages of the prior art.

It is another object of the invention to provide an improved structure of a gas sensor which is compact in size, but possesses high durability and may be manufactured at low costs.

According to one aspect of the invention, there is provided an improved structure of a gas sensor designed to measure a given component content in a gas. The gas sensor comprises: (a) a housing having a first end and a second end; (b) a sensing element disposed in the housing, the sensing element having a base portion and a gas-sensing portion, the base portion projecting from the first end of the housing, the gas-sensing portion projecting from the second end of the housing; (c) a first cover installed on the first end of the housing to cover the base portion of the sensing element; (d) a plurality of electric terminals connected to the sensing element for establishing electric communication between the sensing element and an external device; (e) an insulator in which the electric terminals are disposed, the insulator including a body and a flange, the flange having an groove formed in a peripheral wall thereof; (f) a second cover installed on the second end of the housing to cover the gas-sensing portion of the sensing element and retain the insulator therein, the second cover including a small-diameter portion, a large-diameter portion, and a shoulder connecting between the small-diameter portion and the large-diameter portion, the small-diameter portion being greater in diameter than the body of the insulator and smaller in diameter than the flange of the insulator, the large-diameter portion being greater in diameter than the flange of the insulator; and (g) an elastic holding mechanism disposed between the groove of the flange of the insulator and an inner wall of the large-diameter portion of the second cover to be deformable elastically in a radius direction of the second cover to hold the insulator within the second cover firmly.

In the preferred mode of the invention, the elastic holding mechanism includes a plurality of springs disposed in the groove of the flange at regular intervals away from each other.

Each of the springs is made of a corrugated plate which is disposed between the groove of the flange and the inner wall of the large-diameter portion of the second cover so as to urge the flange of the insulator elastically inwardly of the second cover, thereby holding the insulator within the second cover.

Each of the corrugated plate may have an extension wall which is placed in surface contact with the inner wall of the second cover and welded at a portion thereof to the inner wall of the second cover.

The elastic holding mechanism may alternatively be made of a spring ring disposed in the groove of the flange of the insulator.

The spring ring has disposed on a periphery wall thereof a plurality of members which are so folded as to produce elastic pressure between the flange of the insulator and the inner wall of the second cover for holding the insulator within the second cover firmly.

According to the second aspect of the invention, there is provided a gas sensor measuring a given component content in a gas which comprises: (a) a housing having a first end and a second end; (b) a sensing element disposed in the housing, the sensing element having a base portion and a gas-sensing portion, the base portion projecting from the first end of the housing, the gas-sensing portion projecting from the second end of the housing; (c) a first cover installed on the first end of the housing to cover the base portion of the sensing element; (d) a plurality of electric terminals connected to the sensing element for establishing electric communication between the sensing element and an external device; (e) an insulator in which the electric terminals are disposed, the insulator including a body and a flange; (f) a second cover installed on the second end of the housing to cover the gas-sensing portion of the sensing element and retain the insulator therein, the second cover including a small-diameter portion, a large-diameter portion, and a shoulder connecting between the small-diameter portion and the large-diameter portion, the small-diameter portion being greater in diameter than the body of the insulator and smaller in diameter than the flange of the insulator, the large-diameter portion being greater in diameter than the flange of the insulator; and (g) an elastic holding mechanism disposed in a gap between the insulator and an inner wall of the second cover so as to produce elastic pressure which holds the insulator elastically within the second cover.

In the preferred mode of the invention, the elastic holding mechanism is disposed in the gap between the body of the insulator and an inner wall of the large-diameter portion of the second cover in contact with the body of the insulator and the inner wall of the large-diameter portion of the second cover to urge the flange elastically into constant engagement with an inner wall of the shoulder of the second cover, thereby retaining the insulator within the second cover firmly.

The elastic holding mechanism is made of a ring base and a plurality of elastic deformable members installed on the ring base. Each of the elastic deformable members is placed in contact with the body of the insulator and the inner wall of the large-diameter portion of the second cover to urge the flange elastically into constant engagement with an inner wall of the shoulder of the second cover, thereby retaining the insulator within the second cover firmly.

The elastic holding mechanism may alternatively include a base and an elastically deformable member. The base is placed in contact with one of opposed surfaces of the flange of the insulator remote from an inner wall of the shoulder of the second cover. The elastically deformable member is press fit within the gap between the flange of the insulator and the inner wall of the large-diameter portion of the second cover in surface contact with the inner wall of the large-diameter portion of the second cover to urge the flange inwardly in the radius direction of the second cover elastically, thereby retaining the insulator within the second cover firmly.

The elastic holding mechanism may alternatively include a ring base and an elastically deformable member installed on the ring base. The ring base is placed in contact with one of the opposed surfaces of the flange of the insulator remote from the inner wall of the shoulder of the second cover. The elastically deformable member is press fit within the gap between the flange of the insulator and the inner wall of the large-diameter portion of the second cover to urge the flange inwardly in the radius direction of the second cover elastically, thereby retaining the insulator within the second.

The elastically deformable member may have a V-shape or a U-shape.

The elastic holding mechanism may alternatively include a ring base and a plurality of elastically deformable members installed on the ring. The ring base is placed in contact with one of the opposed surfaces of the flange of the insulator remote from the inner wall of the shoulder of the second cover. The elastically deformable members is press fit within the gap between the flange of the insulator and the inner wall of the large-diameter portion of the second cover to urge the flange inwardly in a radius direction of the second cover elastically, thereby retaining the insulator within the second cover firmly.

The elastic holding mechanism may alternatively include a base and an elastically deformable member extending from the base. The base is placed between the inner wall of the shoulder of the second over and the surface of the flange of the insulator. The elastically deformable member is press fit within the gap between the flange of the insulator and the inner wall of the large-diameter portion of the second cover to urge the flange inwardly in the radius direction of the second cover elastically, thereby retaining the insulator within the second cover firmly.

The elastically deformable member may be made of a corrugated spring plate extending longitudinally of the insulator in contact with the flange of the insulator and the inner wall of the large-diameter portion of the second cover.

The base of the elastic holding mechanism may be made of a ring. The corrugated spring plate is of an annular shape and extends from a periphery of the ring.

The elastic holding mechanism may alternatively include a ring base and elastically deformable corrugated members connected to the ring base. The ring base is placed between the inner wall of the shoulder of the second over and the surface of the flange of the insulator. Each of the elastically deformable corrugated members is press fit within the gap between the flange of the insulator and the inner wall of the large-diameter portion of the second cover to urge the flange inwardly in the radius direction of the second cover elastically, thereby retaining the insulator within the second cover firmly.

The elastic holding mechanism may alternatively include a protrusion provided on an inner wall of the large-diameter portion of the second cover and an elastically deformable member disposed between the protrusion and the surface of the flange of the insulator to urge the flange elastically into constant engagement with the shoulder of the second cover, thereby retaining the insulator within the second cover firmly.

The protrusion is made of a ring connected to the inner wall of the large-diameter portion of the second cover. The elastically deformable member is made of an annular spring which is substantially of S-shape in cross section.

The elastic holding mechanism may alternatively include a plurality of corrugated spring plates and a ridge formed on the inner wall of the large-diameter portion of the second cover on which the flange of the insulator is placed. The corrugated spring plates are disposed in the gap between the inner wall of the shoulder of the second cover and one of the opposed surfaces of the flange to produce elastic pressure which urges the flange elastically against the ridge, thereby holding the insulator within the second over firmly.

The elastic holding mechanism may alternatively include a spring ring having a corrugated shape in cross section and a ridge formed on the inner wall of the large-diameter portion of the second cover on which the flange of the insulator is placed. The spring ring is disposed in the gap between an inner wall of the shoulder of the second cover and one of the opposed surfaces of the flange to produce elastic pressure which urges the flange elastically against the ridge, thereby holding the insulator within the second over firmly.

The elastic holding mechanism may alternatively include a plurality of springs each made up of an outer plate, an inner plate, and a base connecting between the outer and inner plates. The outer plate is in elastic contact with the inner wall of the large-diameter portion of the second over. The inner plate is in elastic contact with an outer wall of the body of the insulator, thereby bringing the base into constant engagement with one of the opposed surfaces of the flange of the insulator to urge the flange elastically against an inner wall of the shoulder of the second cover.

The outer plate may have an extension wall which is placed in surface contact with the inner wall of the second cover and welded at a portion thereof to the inner wall of the second cover.

The elastically deformable member of the elastic holding mechanism may have an extension wall which is placed in surface contact with the inner wall of the second cover and welded at a portion thereof to the inner wall of the second cover.

The elastic holding mechanism may alternatively be made of a spring plate having a first and a second end. The first end is connected to an inner wall of the large-diameter portion of the second cover. The second end is in elastic contact with one of opposed surfaces of the flange of the insulator, thereby urging the flange of the insulator into constant engagement of the other opposed surface of the flange with an inner wall of the shoulder of the second cover.

According to the third aspect of the invention, there is provided a gas sensor measuring a given component content in a gas which comprises: (a) a housing having a first end and a second end; (b) a sensing element disposed in the housing, the sensing element having a base portion and a gas-sensing portion, the base portion projecting from the first end of the housing, the gas-sensing portion projecting from the second end of the housing; (c) a first cover installed on the first end of the housing to cover the base portion of the sensing element; (d) a plurality of electric terminals connected to the sensing element for establishing electric communication between the sensing element and an external device; (e) an insulator in which the electric terminals are disposed, the insulator including a body and a flange; (f) a second cover installed on the second end of the housing to cover the gas-sensing portion of the sensing element and retain the insulator therein, the second cover including a small-diameter portion, a large-diameter portion, and a shoulder connecting between the small-diameter portion and the large-diameter portion, the small-diameter portion being greater in diameter than the body of the insulator and smaller in diameter than the flange of the insulator, the large-diameter portion being greater in diameter than the flange of the insulator; and (g) a holding mechanism disposed between an end of the body of the insulator and the first end of the housing to retain the insulator within the second cover.

In the preferred mode of the invention, the holding mechanism is made of a spring.

The holding mechanism may alternatively be made of a cylindrical rigid member.

According to the fourth aspect of the invention, there is provided a gas sensor measuring a given component content in a gas which comprises: (a) a housing having a first end and a second end; (b) a sensing element disposed in the housing, the sensing element having a base portion and a gas-sensing portion, the base portion projecting from the first end of the housing, the gas-sensing portion projecting from the second end of the housing; (c) a first cover installed on the first end of the housing to cover the base portion of the sensing element; (d) a plurality of electric terminals connected to the sensing element for establishing electric communication between the sensing element and an external device; (e) an insulator in which the electric terminals are disposed, the insulator including a body and a flange; (f) a second cover installed on the second end of the housing to cover the gas-sensing portion of the sensing element and retain the insulator therein, the second cover including a small-diameter portion, a large-diameter portion, and a shoulder connecting between the small-diameter portion and the large-diameter portion, the small-diameter portion being greater in diameter than the body of the insulator and smaller in diameter than the flange of the insulator, the large-diameter portion being greater in diameter than the flange of the insulator; and (g) a holding member holding the insulator within the second cover, the holding member being made of a wedge-shaped member and fitted between the flange of the insulator and an inner wall of the large-diameter portion of the second cover to retain the insulator firmly.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 16 is a partially vertical sectional view which shows an insulator-holding member according to the sixth embodiment of the invention;

FIG. 17(a) is a partially vertical sectional view which shows a modification of the structure of FIG. 16;

FIG. 17(b) is a perspective view which shows an insulator-holding member of FIG. 17(a);

FIG. 19(a) is a partially vertical sectional view which shows a mount structure of an insulation porcelain according to the eighth embodiment of the invention;

FIG. 19(b) is a partially perspective view which shows the mount structure of FIG. 19(a);

FIG. 22(a) is a partially vertical sectional view which shows the tenth embodiment of the invention which is a modification of the first embodiment shown in FIGS. 1 to 3(c);

FIG. 22(b) is a partially vertical sectional view which shows the tenth embodiment of the invention which is a modification of the third embodiment shown in FIGS. 7(a) to 7(c);

FIG. 23(a) is a partially vertical sectional view which shows a modification of the fourth embodiment as shown in FIGS. 9(a) and 9(b);

FIG. 23(b) is a partially vertical sectional view which shows a modification of the fifth embodiment shown in FIGS. 13(a) and 13(b);

DESCRIPTION OF THE PREFERRED EMBODIMENTS

Figure 1:
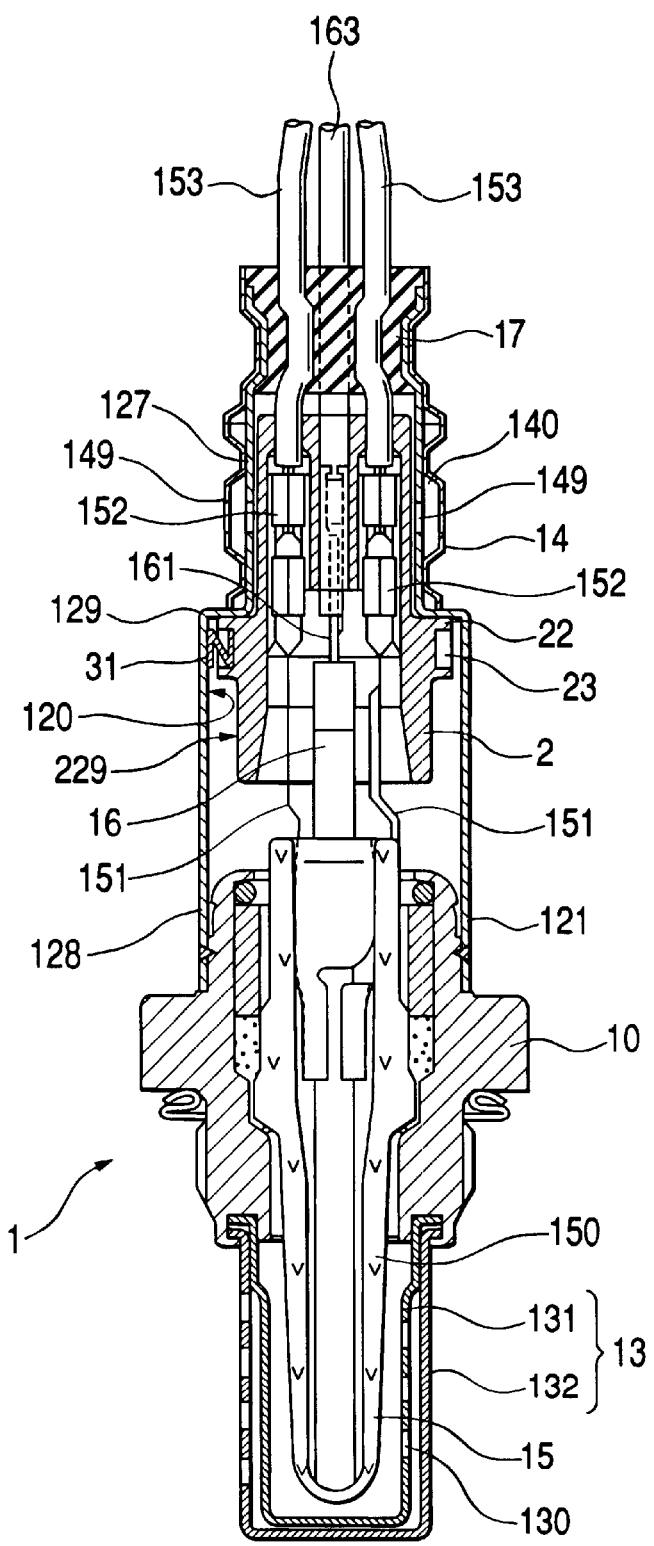
FIG. 1 is a longitudinal sectional view which shows a gas sensor according to the first embodiment of the invention.

Referring to the drawings, wherein like reference numbers refer to like parts in several views, particularly to FIGS. 1 to 5, there is shown a gas sensor 1 according to the first embodiment of the invention which is designed to be installed in an exhaust system of an automotive internal combustion engine to measure an oxygen content in exhaust gasses. Note that the present invention is not limited to an oxygen sensor and may alternatively be used with a variety of gas sensors such as HC, CO, and NOx sensors.

The gas sensor 1 generally includes a sensing element 15, a hollow cylindrical housing 10, a measured gas cover assembly 13, terminals 151 electrically leading to the sensing element 15, an insulation porcelain 2, and an air cover 121. The sensing element 15 is retained in the housing 10 and surrounded at a head (i.e., a gas-sensing portion) thereof by the measured gas cover assembly 13. The insulation porcelain 2 insulates the terminals 151 from each other. The air cover 121 is installed at an end thereof on a flange of the housing 10 and covers the insulation porcelain 2 and a base of the sensing element 15.

Figure 2:
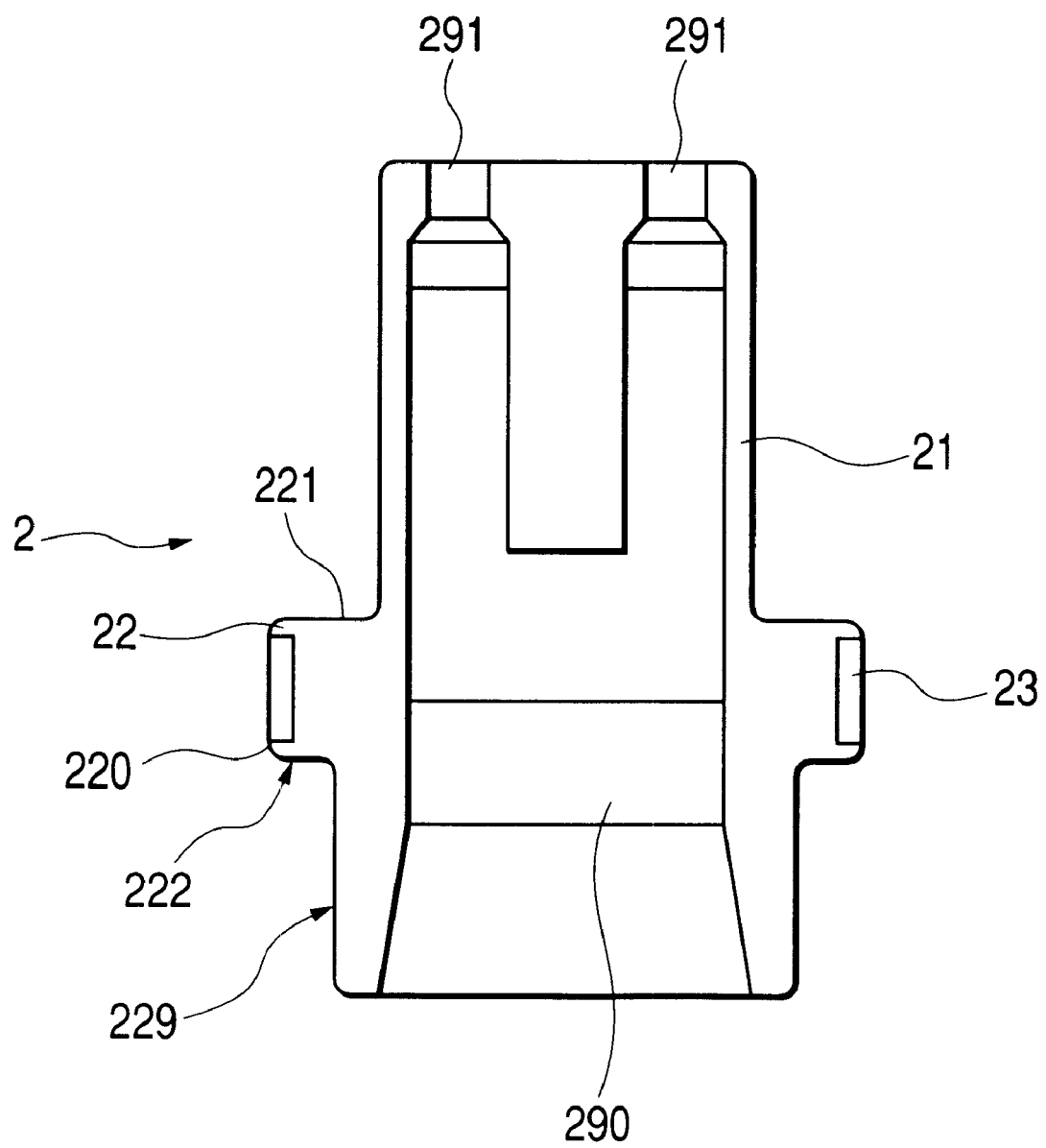
FIG. 2 is a longitudinal sectional view which shows an insulation porcelain installed in the gas sensor of FIG. 1.

The insulation porcelain 2 is made of a hollow cylindrical member which, as clearly shown in FIG. 2, consists of a body 21 and a flange 22. The air cover 121 has, as shown in FIG. 1, a small-diameter portion 127, a large-diameter portion 128, and a shoulder 129. The small-diameter portion 127 has an inner diameter which is greater than an outer diameter of the body 21 of the insulation porcelain 2 and smaller than an outer diameter of the flange 22 of the insulation porcelain 2. The large-diameter portion 128 has an inner diameter greater than the outer diameter of the flange 22. The shoulder 129 is formed between the small-diameter portion 127 and the large-diameter portion 128.

The insulation porcelain 2 has, as shown in FIGS. 1 and 2, a groove 23 formed in a peripheral surface 220 of the flange 22. Holding members 31, as will be described later in detail, are disposed within the groove 23 of the insulation porcelain 2 in elastic contact with an inner wall of the air cover 121. The holding members 31 are each made of a spring designed to expand and contract in a radius direction of the air cover 121.

The measured gas cover assembly 13 is, as described above, installed at an end thereof in an groove formed in the bottom of the housing 10. The measured gas cover assembly 13 is made up of an inner cover 131 and an outer cover 132 both of which have gas inlets 130 through which the gas to be measured is admitted into a gas chamber defined around the sensing element 15.

The air cover 121 is welded to a base portion of the housing 10. An outer air cover 14 is installed around the small-diameter portion 127 of the air cover 121 through a cylindrical water-repellent filter 140. The air cover 121 and the outer air cover 14 have formed therein air vents 149 which lead to a reference gas chamber defined in the sensing element 15 for inducting the air into the reference gas chamber.

An elastic insulator 17 is fitted within an open end portion of the air cover 121 which holds a pair of leads 153 and a pair of leads 163 (only one is shown in FIG. 1 for the brevity of illustration) in holes formed therein. The leads 163 are connected to a heater 16 through connectors 161 for supplying the power thereto. The leads 153 are connected to the sensing element 15 to provide sensor signals to an external device which are used in determining the concentration of oxygen contained in a gas. This technique is well known in the art, and explanation thereof in detail will be omitted here. For instance, U.S. Pat. No. 6,222,372, assigned to the same assignee as that of this application teaches, a gas measuring method in this type of gas sensor, the disclosure of which is incorporated herein by reference.

The sensing element 15 is made of a cup-shaped solid electrolyte body 150 which defines therein the reference gas chamber as described above. The heater 16 is made of a bar-shaped resistance member and disposed within the reference gas chamber for heating measuring and reference electrodes formed on the sensing element 15 up to a temperature at which the oxygen concentration can be measured correctly. The measuring and reference electrodes are connected to the terminals 151, respectively. The terminals 151 are connected to the leads 153 through connectors 152, respectively.

The insulation porcelain 2 which is made of a ceramic material (alumina) is, as described above, disposed within the air cover 121. The insulation porcelain 2, as clearly shown in FIG. 2, has formed therein four through holes 291 into which the leads 153 and 163 are inserted and a cavity 290 which communicates with the through holes 291 and opens downward, as viewed in the drawing. Within the cavity 290, the base of the sensing element 15 is disposed.

The insulation porcelain 2 has, as already described, the flange 22. The annular groove 23 is formed in the peripheral wall of the flange 22. The holding members 31 are installed in the grooves 23 to retain the insulation porcelain 2 within the air cover 121, as will be described in detail below. The holding members 31 are each made of a heat-resisting metal such as stainless steel. Instead of the annular groove 23, discrete recesses may be formed in the periphery of the flange 22.

Figure 3A:
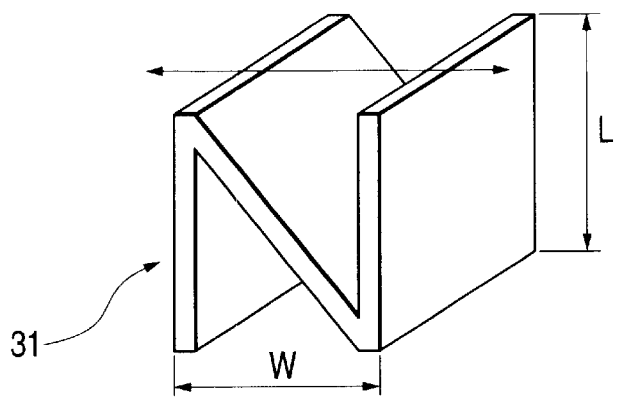
FIG. 3(a) is a perspective view which shows a holding member used to retain the insulation porcelain of FIG. 2 in the gas sensor of FIG. 1.
Figure 3B:
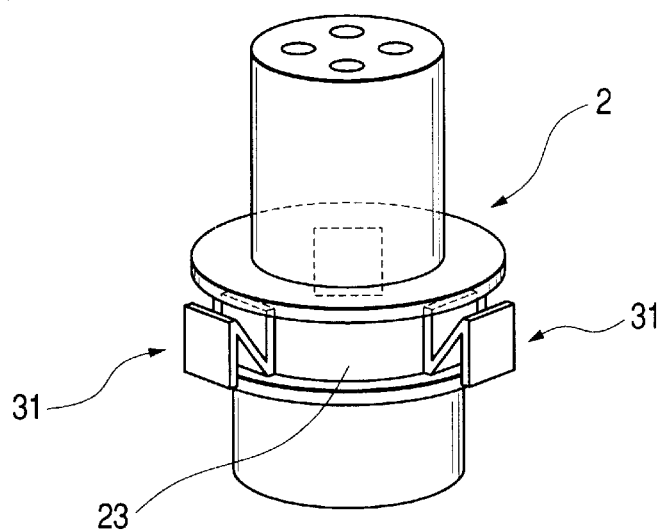
FIG. 3(b) is a perspective view which shows holding members fitted in the insulation porcelain of FIG. 2.

Each of the holding members 31 is, as shown in FIG. 3(a), implemented by an N-shaped spring plate which is so designed as to deformable elastically in a direction, as indicated by an arrow. The three holding members 31 are, as can be seen in FIG. 3(b), disposed in the groove 23 at regular intervals. Each of the holding members 31 is fitted within the groove 23 in contact with upper and lower walls of the groove 23 in order to avoid undesirable play in a vertical direction, as viewed in the drawing (i.e., a width-wise direction of the groove 23). Specifically, the length L of the holding members 31, as shown in FIG. 3(a), is set substantially equal to the width of the groove 23.

The width W of the holding members 31 when subjected to no load is set greater than the interval between the bottom of the groove 23 and the inner wall 120 of the air cover 121.

Figure 3C:
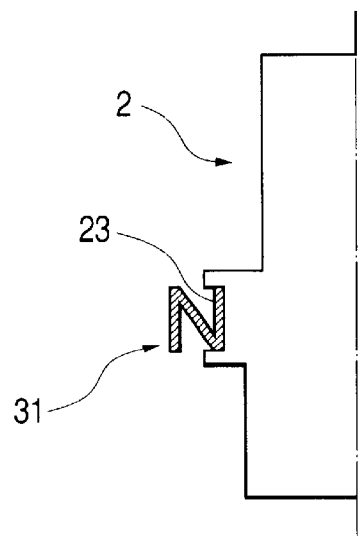
FIG. 3(c) is a partial sectional view which shows a holding member fitted in a groove formed in a flange of the insulation porcelain shown in FIG. 3(b)

The installation of the insulation porcelain 2 in the air cover 121 is accomplished by placing the holding members 31 in the groove 23, as shown in FIGS. 3(b) and 3(c), compressing the holding members 31 inwardly of the insulation porcelain 2, and inserting the insulation porcelain 2 into the air cover 121. Upon insertion of the insulation porcelain 2, spring pressures are produced by the holding members 31 which are oriented in the radius direction of the air cover 121 to retain the insulation porcelain 2 in the air cover 121 in elastic engagement with the inner wall 120 of the air cover 121.

The holding members 31 are, as described above, made of a spring and thus need not be formed with high dimensional accuracy. Accumulated dimensional errors of the groove 23, the insulation porcelain 2, and the air cover 121 in the radius direction of the gas sensor 1 are absorbed by the elasticity of the holding members 31, thus eliminating the need for machining those parts with high dimensional accuracy and resulting in an increase in durability of the gas sensor 1. The gas sensor 1 may thus be fabricated easily at low costs.

Figure 25:
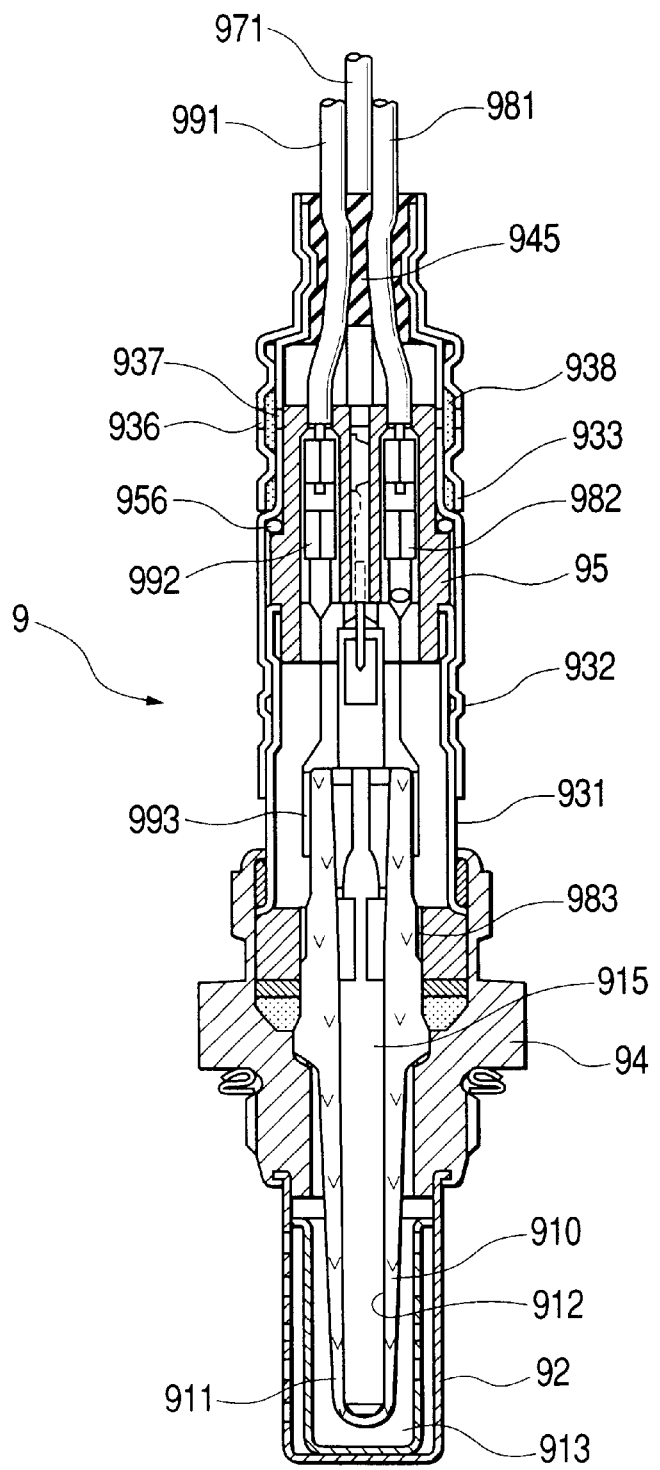
FIG. 25 is a longitudinal sectional view which shows a conventional gas sensor.

Moreover, the installation of the insulation porcelain 2 within the single-walled air cover 121 allows the overall length of the gas sensor 1 to be decreased as compared with the conventional structure shown in FIG. 25.

Figure 4:
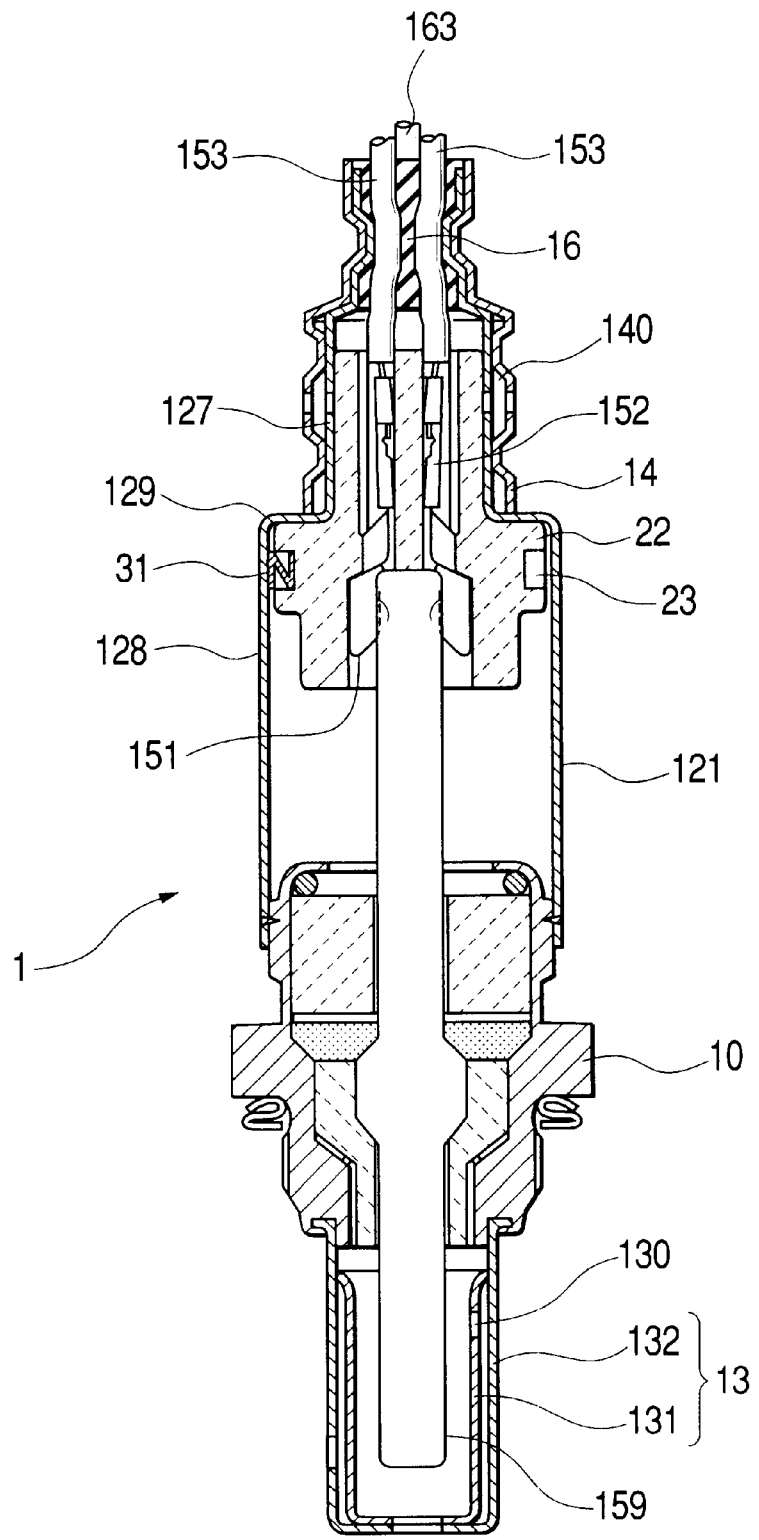
FIG. 4 is a vertical sectional view which shows another type of a gas sensor with which the holding member in FIGS. 1 to 3(c) may be used.

The sensing element 15 may be replaced with another type of element such as one indicated at 159 in FIG. 4 which is made of a lamination of a heater layer and electrode layers. U.S. Pat. No. 5,573,650, issued on Nov. 12, 1996 to Fukaya et al. teaches such a structure, disclosure of which is incorporated herein by reference.

Figure 5:
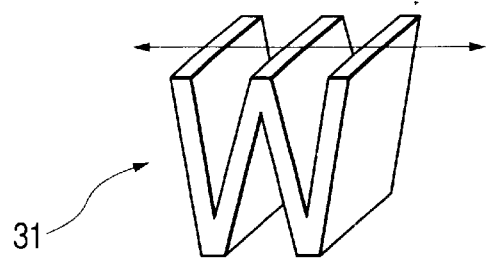
FIG. 5 is a perspective which shows a modification of a holding member of the first embodiment.

The holding members 31 may alternatively be, as shown in FIG. 5, made of a W-shaped spring strip which is so designed as to expand and contract in a direction as indicated by an arrow.

Figure 6A:
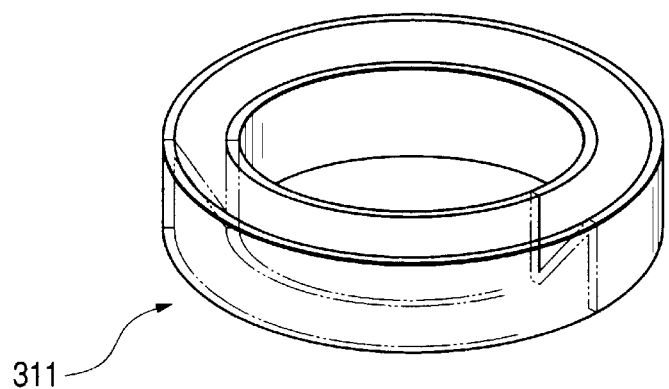
FIG. 6(a) is a perspective view which shows a holding member according to the second embodiment of the invention.

FIG. 6(a) shows the second embodiment of the invention in which a holding member 311 is used instead of the holding members 31 in the first embodiment.

The holding member 311 is made of a single ring which is folded to have, like the first embodiment, an N-shape in cross section.

Figure 6B:
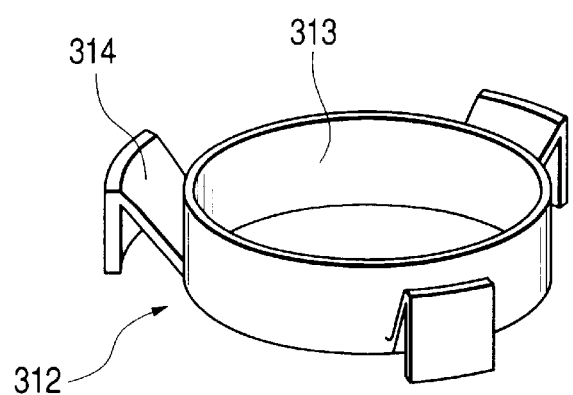
FIG. 6(b) is a perspective view which shows a modification of the holding member of FIG. 6(a)

A holding member 312, as shown in FIG. 6(b), may alternatively be used which consists of a ring 313 and three V-shaped spring plates 314. The spring plates 314 are joined to the periphery of the ring 313 at regular intervals to possess the elasticity in a radius direction of the ring 313.

Other arrangements are identical with those of the first embodiment, and explanation thereof in detail will be omitted here.

Figure 7A:
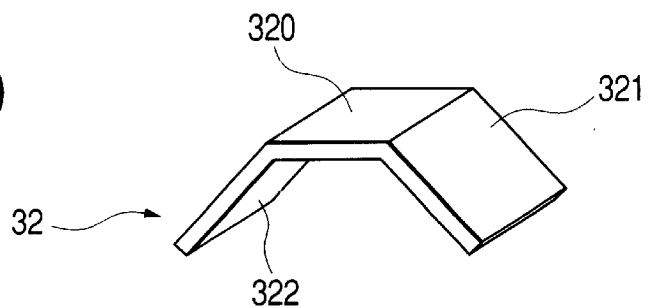
FIG. 7(a) is a perspective view which shows a holding member according to the third embodiment of the invention.
Figure 7B:
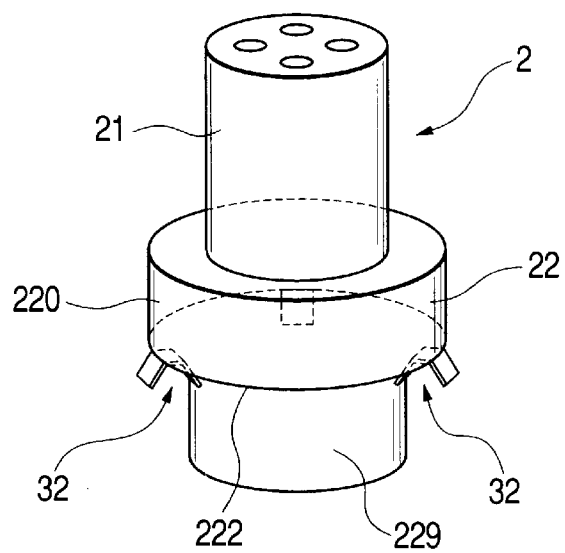
FIG. 7(b) is a perspective view which shows holding members attached to an insulation porcelain in the third embodiment.
Figure 7C:
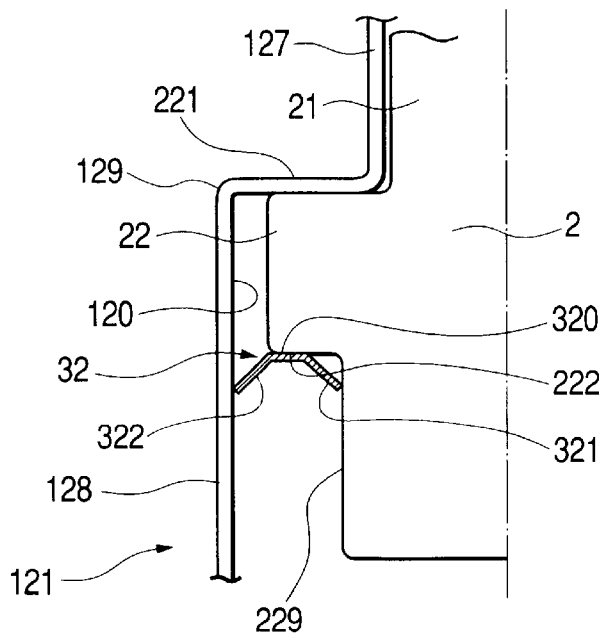
FIG. 7(c) is a partially vertical sectional view which shows installation of the insulation porcelain of FIG. 7(b) in an air cover of a gas sensor.

FIGS. 7(a) to 7(c) show the third embodiment of the invention.

The insulation porcelain 2 does not have the groove 23 formed in the flange 22 in the first embodiment and is, as clearly shown in FIG. 7(c), retained within the air cover 121 by three holding members 32.

Each of the holding members 32 is made of substantially a C-shaped spring strip which consists of a base 320, an inner claw 321, and an outer claw 322. The inner and outer claws 321 and 322 are bent from ends of the base 320 in the same direction.

The insulation porcelain 2 is, like the first embodiment, installed within the air cover 121. The holding members 32 are, as shown in FIG. 7(b), disposed on a lower surface 222 of the flange 22 at regular intervals and elastically fitted in a gap between the large-diameter portion 229 of the insulation porcelain 2 and the inner wall 120 of the air cover 121. Specifically, the inner claw 321 of each of the holding members 32 extends from the base 320 downward and to the left, as viewed in FIG. 7(c), and elastically engages the large-diameter portion 229 of the insulation porcelain 2, while the outer claw 322 extends from the base 320 downward and to the right and elastically engages the inner wall 120 of the air cover 121, thereby producing a horizontal spring pressure to hold the insulation porcelain 2 in the radius direction of the air cover 121 and a vertical spring pressure to urge the flange 22 into constant engagement of the upper surface 221 with the inner wall of the shoulder 129 of the air cover 121, thereby holding the insulation porcelain 2 in a longitudinal direction of the air cover 121.

The installation of the insulation porcelain 2 is accomplished by inserting the insulation porcelain 2 into the air cover 121 and forcing the holding members 32 into the gap between the inner wall 120 of the air cover 121 and the large-diameter portion 229 of the insulation porcelain 2 to hold the flange 22 between the base 320 of each of the holding members 32 and the shoulder 129 of the air cover 121.

Like the first embodiment, accumulated dimensional errors of the insulation porcelain 2 and the air cover 121 in the radius direction of the gas sensor 1 are absorbed by the elastic deformation of the inner and outer claws 321 and 322 of the holding members 32 when fitted in the air cover 121, thus eliminating the need for machining those parts with high dimensional accuracy, resulting in ease of fabrication of the gas sensor 1.

Figure 8:
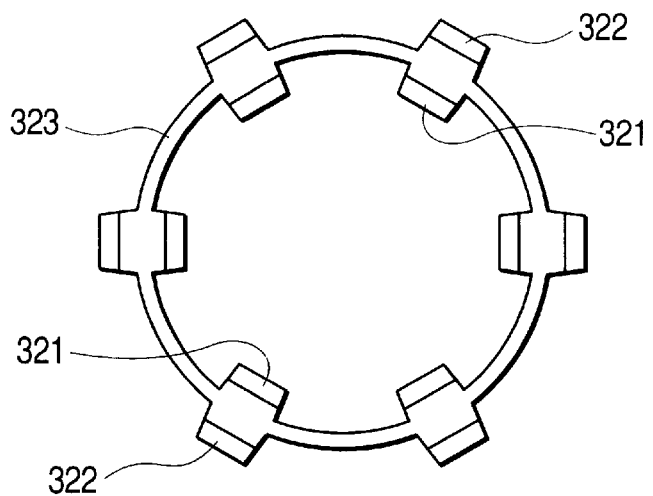
FIG. 8 is a plane view which shows a modification of the third embodiment shown in FIGS. 7(a) to 7(c)

Instead of the holding members 32, a one-piece holding member, as shown in FIG. 8, may be used which consists of a ring 323 and inner and outer claws 321 and 322. The inner and outer claws 321 and 322 extend from the ring 323 diagonally in the same direction, like the ones shown in FIG. 7(a).

Figure 9A:
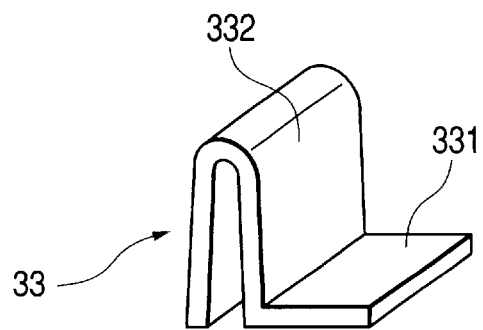
FIG. 9(a) is a perspective view which shows a holding member in the fourth embodiment of the invention.
Figure 9B:
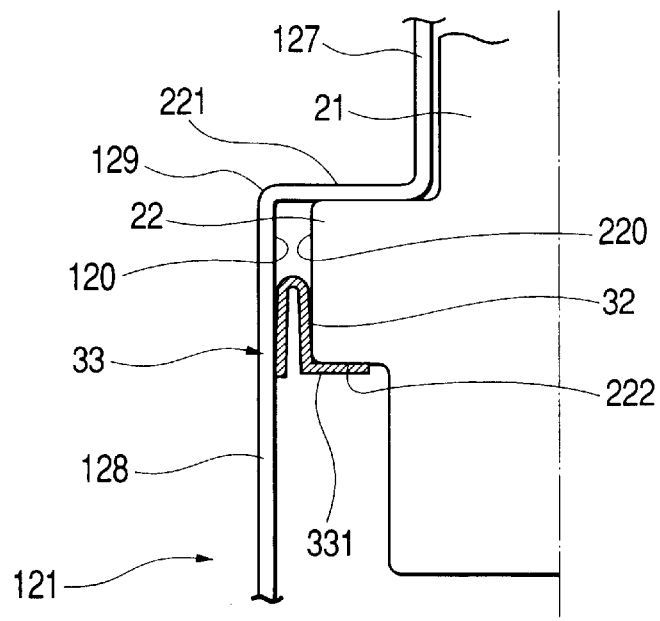
FIG. 9(b) is a partial sectional view which shows installation of the holding member of FIG. 9(a)

FIGS. 9(a) and 9(b) show the fourth embodiment of the invention which is different from the third embodiment of FIGS. 7(a) and 7(b) only in that three holding members 33 are fitted within a gap between the flange 22 and the inner wall 120 of the air cover 121 at regular intervals. Other arrangements are identical, and explanation thereof in detail will be omitted here.

Each of the holding members 33 consists of a base 331 and a U-shaped elastic portion 332 projecting vertically from the base 331. A total thickness of the elastic portion 332 is slightly greater than the interval between the peripheral surface 220 of the flange 22 and the inner wall 120 of the air cover 121 so as to produce the spring pressure in the radius direction of the insulation porcelain 2 when installed in the air cover 121.

The elastic portion 332 of each of the holding members 33 is press fit within the gap between the peripheral surface 220 of the flange 22 and the inner wall 120 of the air cover 121 to hold the insulation porcelain 2 in the radius direction of the air cover 121, while the base 331 engages the lower surface 222 of the flange 22 to urge the flange 22 into constant engagement of the upper surface 221 with the inner wall of the shoulder 129 of the air cover 121, thereby holding the insulation porcelain 2 in the longitudinal direction of the air cover 121.

In this embodiment, the elastic portion 332 of each of the holding members 33 has wider contact areas with the inner wall 120 of the air cover 121 and the peripheral surface 220 of the flange 22, thereby producing a greater frictional pressure between the inner wall 120 of the air cover 121 and the peripheral surface 220 of the flange 22 to retain the insulation porcelain 2 firmly.

The installation of the insulation porcelain 2 is accomplished in the following manner. First, each of the holding members 33 is joined to the flange 22 in engagement of the base 331 and the elastic portion 332 with the lower surface 222 and the peripheral surface 220 of the flange 22, respectively. Next, the insulation porcelain 2 is forced into the air cover 121 until the flange 22 hits on the shoulder 129 of the air cover 121.

Like the above embodiments, a total dimensional error of the insulation porcelain 2 and the air cover 121 in the radius direction of the gas sensor 1 is absorbed by the elastic deformation of the elastic portions 332 of the holding members 32 when fitted in the air cover 121, thus eliminating the need for machining those parts with high dimensional accuracy, resulting in ease of fabrication of the gas sensor 1. Moreover, the installation of the insulation porcelain 2 within the single-walled air cover 121 allows the overall length of the gas sensor 1 to be decreased as compared with the conventional structure shown in FIG. 25.

Figure 10:
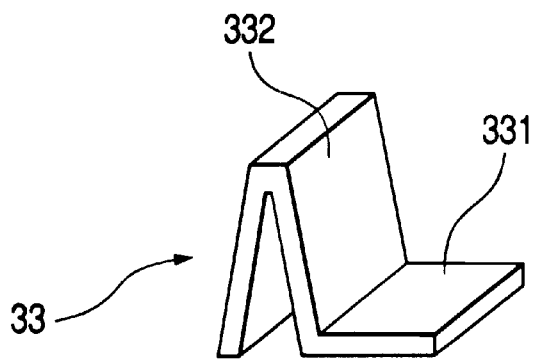
FIG. 10 is a perspective view which shows a modification of the holding member shown in FIG. 9(a)

The elastic portion 332 of each of the holding members 33 may alternatively be machined, as shown in FIG. 10, to a V-shape.

Figure 11A:
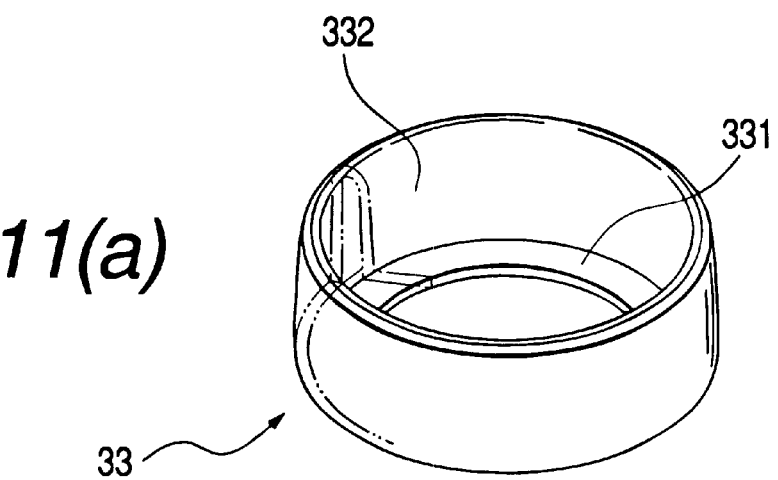
FIGS. 11(a) and 11(b) show modifications of a holding member in the fourth embodiment.
Figure 11B:
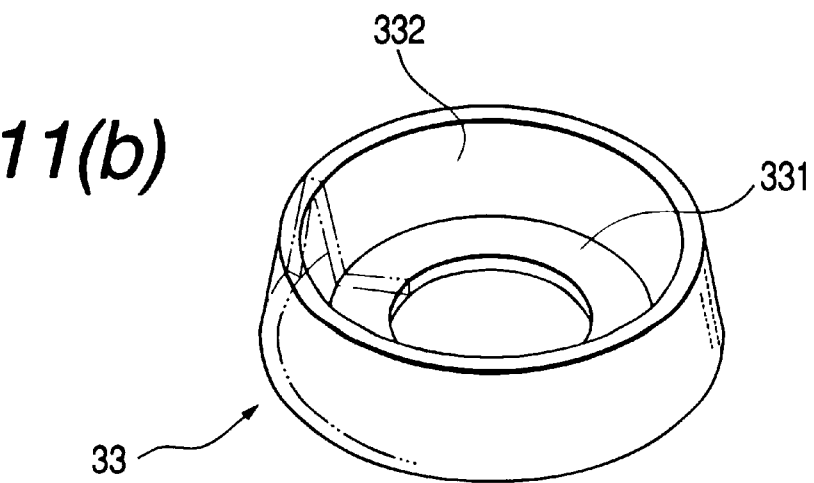

Instead of the holding members 33, a one-piece holding member, as shown in FIG. 11(a) or 11(b), may be used. The holding member of FIG. 11(a) consists of a ring-shaped disc 331 and a double-walled annular member 332. The annular member 332 is, like the one shown in FIG. 9(a), of a U-shape in cross section. The holding member of FIG. 11(b) is different from the one shown in FIG. 11(b) only in that the annular member 332 is of a V-shape in cross section.

Figure 12:
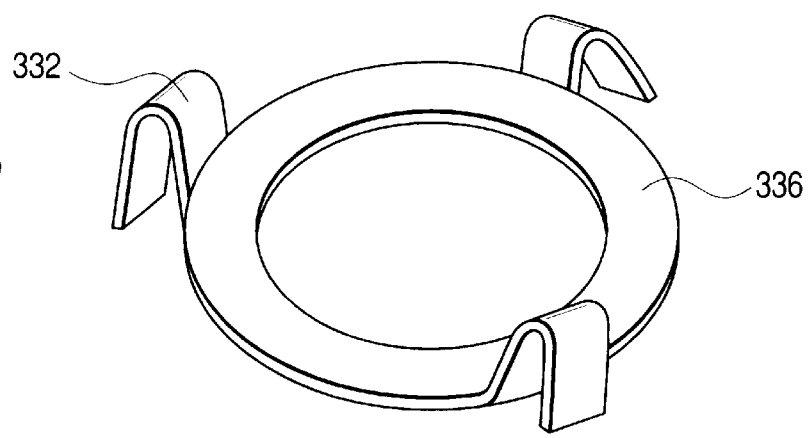
FIG. 12 is a perspective view which shows a modification of a holding member in the fourth embodiment.

The bodies 331 of the holding members 33 in FIGS. 9(a) and 9(b) may alternatively be formed, as shown in FIG. 12, integrally with a ring-shaped disc 336.

Figure 13A:
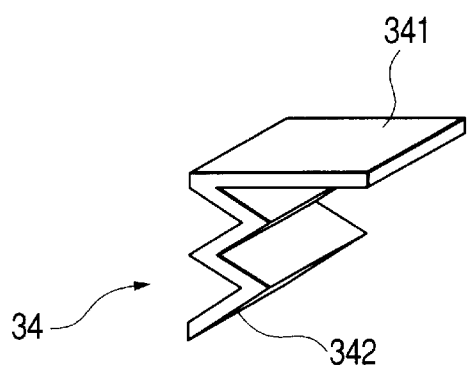
FIG. 13(a) is a perspective view which shows a holding member in the fifth embodiment of the invention.
Figure 13B:
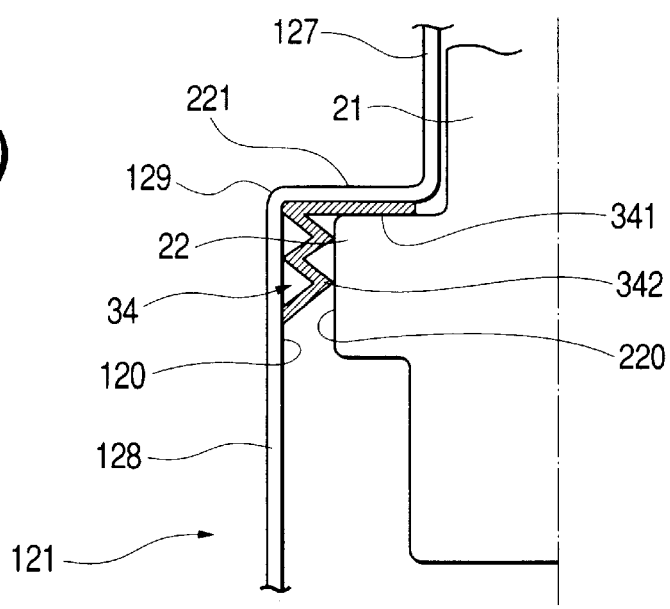
FIG. 13(b) is a partial sectional view which shows installation of the holding member of FIG. 13(a)

FIGS. 13(a) and 13(b) show the fifth embodiment of the invention which is different from the fourth embodiment of FIGS. 9(a) and 9(b) in configuration of holding members. Other arrangements are identical, and explanation thereof in detail will be omitted here.

Three holding members 34 are used to retain the insulation porcelain 2 within the air cover 121. Each of the holding members 34 consists of a flat base 341 and a W-shaped elastic portion 342 extending vertically from the base 341. The flat base 341 is, as clearly shown in FIG. 13(b), held between the upper surface 221 of the flange 22 and the inner wall of the shoulder 129. The elastic portion 342 is formed by waving a portion of the holding member 34 to be deformable elastically in the longitudinal direction of the insulation porcelain 2 (i.e., a vertical direction as viewed in FIGS. 13(a) and 13(b)) and press fit within a gap between the peripheral surface 220 of the flange 22 and the inner wall 120 of the air cover 121 so as to produce the spring pressure in the radius direction of the insulation porcelain 2, thereby holding the insulation porcelain 2 within the air cover 121 firmly.

The installation of the insulation porcelain 2 is accomplished in the following manner. First, each of the holding members 34 is attached to the flange 22 of the insulation porcelain 2 in engagement of the base 341 and the elastic portion 342 with the upper surface 221 and the peripheral surface 220 of the flange 22, respectively. Next, the insulation porcelain 2 is forced into the air cover 121 until the flange 22 hits on the shoulder 129 of the air cover 121.

Like the above embodiments, a total dimensional error of the insulation porcelain 2 and the air cover 121 in the radius direction of the gas sensor 1 is absorbed by the elastic deformation of the elastic portions 342 of the holding members 34 when fitted in the air cover 121, thus eliminating the need for machining those parts with high dimensional accuracy, resulting in ease of fabrication of the gas sensor 1. Moreover, the installation of the insulation porcelain 2 within the single-walled air cover 121 allows the overall length of the gas sensor 1 to be decreased as compared with the conventional structure shown in FIG. 25.

The base 341 of each of the holding members 34 is, as described above, interposed between the shoulder 129 of the air cover 121 and the upper surface 221 of the flange 22 of the insulation porcelain 2, thereby defining gaps therebetween which work as air passages establishing communication between the air vents 149 and the reference chamber within the sensing element 15, thus facilitating ease of air flow into the reference chamber.

Figure 14:
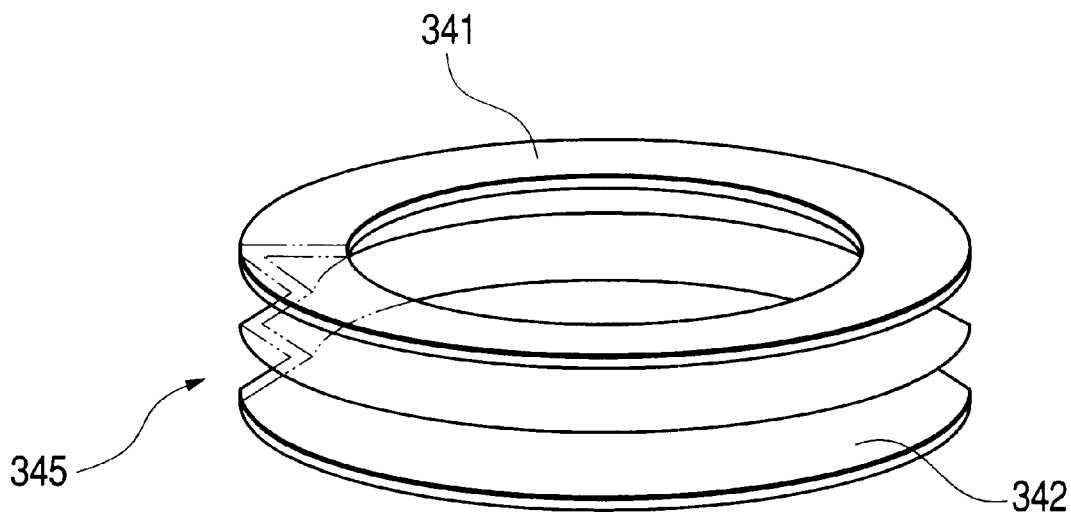
FIG. 14 is a perspective view which shows a modification of a holding member in the fifth embodiment.
Figure 15:
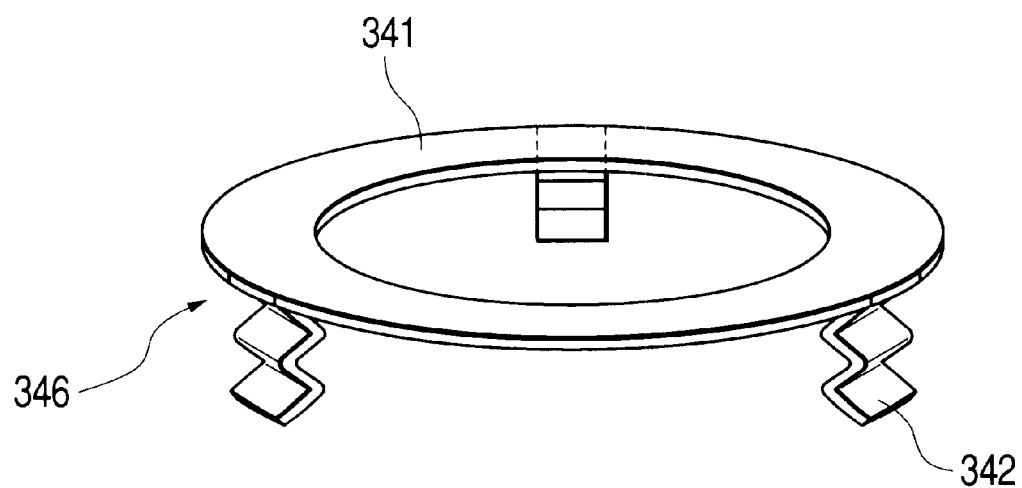
FIG. 15 is a perspective view which shows another modification of a holding member in the fifth embodiment.

Instead of the holding members 34, a holding member 345, as shown in FIG. 14, or a holding member 346, as shown in FIG. 15, may be used. The holding member 345 is made of a one-piece cylindrical member which consists of a ring-shaped base 341 and an accordion-folded annular elastic portion 342. The holding member 346 consists of a ring-shaped base 341 and three W-shaped spring plates 342 attached to the periphery of the base 341 at regular intervals.

FIG. 16 shows the sixth embodiment of the invention.

The insulation porcelain 2 has substantially the same structure as that in the first embodiment except that the groove 23 is not formed in the flange 22.

A holding member 351 which is made of a coil spring is disposed vertically within the air cover 121 to retain the insulation porcelain 2 firmly. Specifically, the holding member 351 is fitted at one end on the large-diameter portion 229 of the insulation porcelain 2 and attached at the other end to the upper end of the housing 10 to urge the flange 22 elastically into constant engagement with the inner wall of the shoulder 129 of the air cover 121.

The installation of the insulation porcelain 2 is accomplished by fitting the holding member 351 fixed on the upper end of the housing 10 on the large-diameter portion 229 of the insulation porcelain 2, inserting these into the air cover 121, and joining the housing 10 and the air cover 121 together. This facilitates ease of fabrication of the gas sensor 1, thereby resulting in a decrease in manufacturing cost.

The use of the single holding member 351 for installation of the insulation porcelain 2 results in an increase in durability of the gas sensor 1. Moreover, the installation of the insulation porcelain 2 within the single-walled air cover 121 allows the overall length of the gas sensor 1 to be decreased as compared with the conventional structure shown in FIG. 25.

Instead of the holding member 351, a rigid holding member 352, as shown in FIG. 17(b), may be used. The holding member 352 is made of a metallic or ceramic hollow cylinder. The holding member 352 is, as clearly shown in FIG. 17(a), fitted at one end on the large-diameter portion 229 of the insulation porcelain 2 in contact with the lower surface 222 of the flange 22 and placed at the other end on the upper end of the housing 10 to bring the flange 22 into constant engagement with the shoulder 129 of the air cover 121.

Figure 18A:
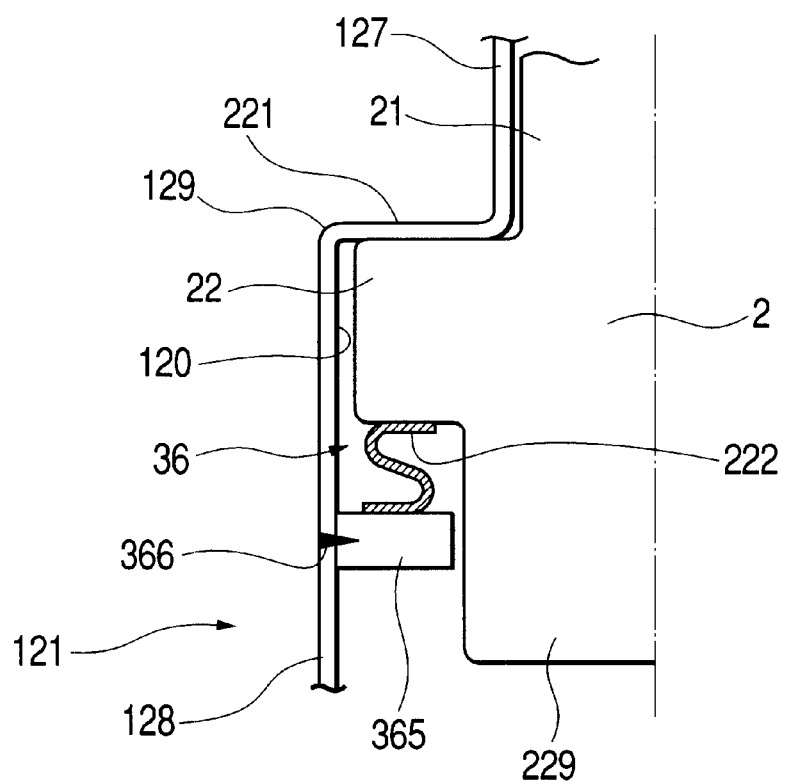
FIG. 18(a) is a partially vertical sectional view which shows a mount structure of an insulation porcelain according to the seventh embodiment of the invention.

FIG. 18(a) shows the seventh embodiment of the invention.

Figure 18B:
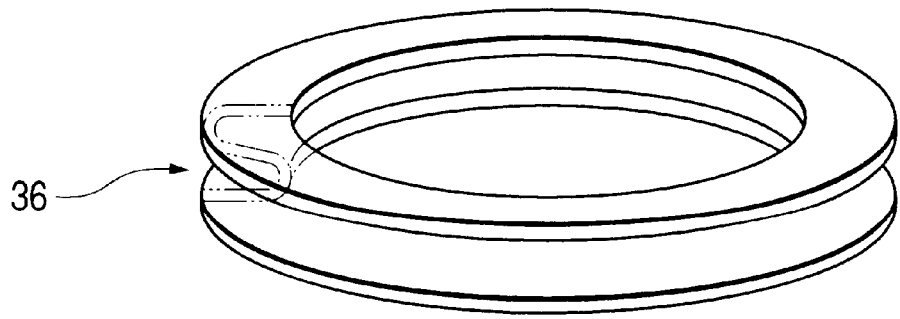
FIG. 18(b) is a perspective view which shows an annular support member for installation of the insulation porcelain in FIG. 18(a)

A ring-shaped mount base 366 is welded at a portion, as indicated at 366, to the inner wall of the air cover 121 within a gap between the large-diameter portion 229 and the inner wall 120 of the air cover 121. A holding member 36 which is, as shown in FIG. 18(b), made of an annular spring having an S-shape in cross section is disposed between the mount base 366 and the lower surface of the flange 22 of the insulation porcelain 2 to urge the flange 22 elastically into constant engagement with the inner wall of the shoulder 129 of the air cover 121, thereby retaining the insulation porcelain 2 in the air cover 121 firmly. The holding member 36 also works to absorb vertical vibrations of the insulation porcelain 2 within the air cover 121, thereby resulting in an increase in total durability of the gas sensor 1.

The installation of the insulation porcelain 2 within the air cover 121 is accomplished by placing the insulation porcelain 2 in contact of the flange 22 with the shoulder 129, putting the holding member 36 on the lower surface 222 of the flange 22, forcing the mount base 366 into the gap between the large-diameter portion 229 of the insulation porcelain 2 and the inner wall of the air cover 121 against the spring pressure of the holding member 36, and welding the mount base 366 to a given portion of the large-diameter portion 128 of the air cover 121, thereby retaining the insulation porcelain 2 within the air cover 121 firmly.

Each of the holding member 36 and the mount base 366 may alternatively be made up of a plurality of elements.

Other arrangements and effects of this embodiment are identical with those in the sixth embodiment, and explanation thereof in detail will be omitted here.

FIGS. 19(a) and 19(b) show the eighth embodiment of the invention.

Three holding members 37 (only one is shown for the brevity of illustration) are disposed at regular intervals between the upper surface 221 of the flange 22 of the insulation porcelain 2 and the inner wall of the shoulder 129 of the air cover 121. Each of the holding members 37 is made of a corrugated plate and designed to be deformable elastically between the upper surface 221 of the flange 22 and the shoulder 129 vertically, as viewed in the drawings. The large-diameter portion 128 of the air cover 121 has formed on the inner wall thereof an annular ridge 375 projecting inwardly. The flange 22 of the insulation porcelain 2 is placed at a corner thereof on the annular ridge 375 against the spring force of the holding members 37, thereby retaining the insulation porcelain 2 within the air cover 121 firmly. The holding members 37 also work to absorb vertical vibrations of the insulation porcelain 2 within the air cover 121, thereby resulting in an increase in total durability of the gas sensor 1.

Instead of the annular ridge 375, a plurality of discrete ridges may be formed on the inner wall of the large-diameter portion 128 of the air cover 121.

The installation of the insulation porcelain 2 within the air cover 121 is accomplished by placing the holding members 37 on the inner wall of the shoulder 129, inserting the insulation porcelain 2 into the air cover 121 against the spring pressure of the holding members 37, and pressing the large-diameter portion 128 of the air cover 121 inwardly to form the annular ridge 375, thereby holding the flange 22 elastically against the spring pressure of the holding members 37.

Other arrangements and effects of this embodiment are identical with those in the sixth embodiment, and explanation thereof in detail will be omitted here.

Figure 20:
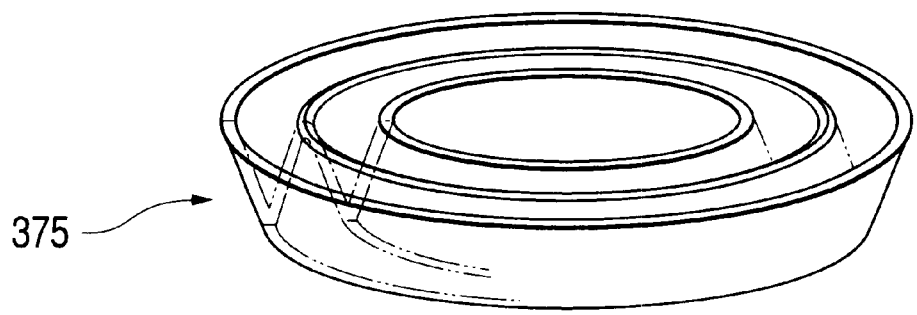
FIG. 20 is a perspective view which shows another holding member which may be used in the mount structure in FIGS. 19(a) and 19(b)

Instead of the holding members 37, an annular holding member 375, as shown in FIG. 20, may be used which is made by pressing an annular plate to a W-shape in cross section.

Figure 21:
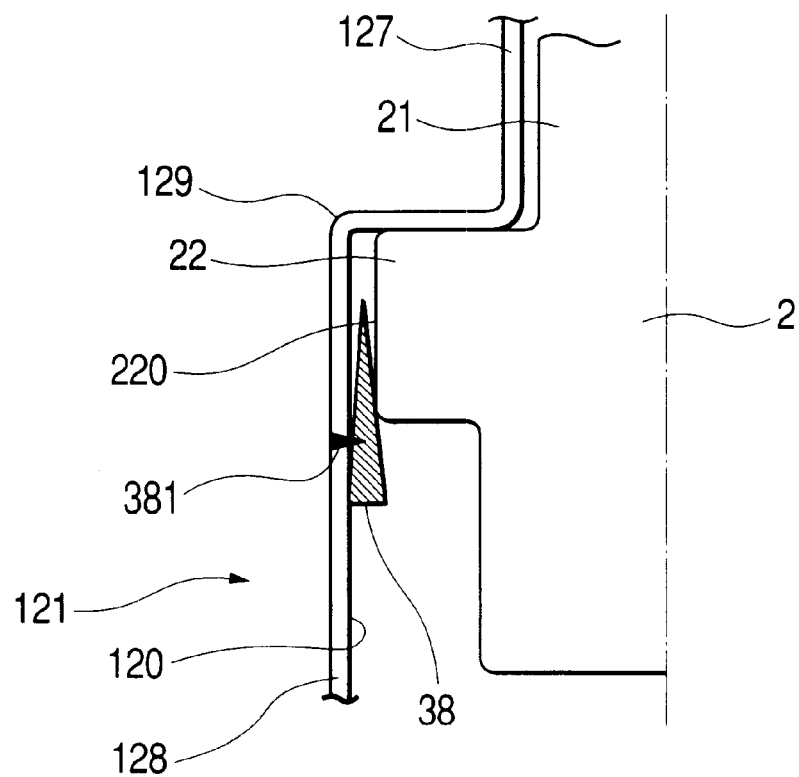
FIG. 21 is a partially vertical sectional view which shows holding members for installation of an insulation porcelain within an air cover according to the ninth embodiment of the invention.

FIG. 21 shows the ninth embodiment of the invention.

A holding member 38 (only one is shown for the brevity of illustration) which is made of a wedge-shaped ring is press fit within a gap between the inner wall 120 of the air cover 121 and the peripheral surface 220 of the flange 22 so as to bring the flange 22 into constant engagement with the inner wall of the shoulder 129 of the air cover 121 and welded, as indicated at 381, to the inner wall 120.

The holding member 38 is in contact with the inner wall 120 of the air cover 121 and the peripheral surface 220 of the flange 22, thereby producing a frictional pressure therebetween to retain the insulation porcelain 2 firmly.

The holding member 38 may alternatively be formed by a plurality of discrete wedges.

Other arrangements and effects of this embodiment are identical with those in the sixth embodiment, and explanation thereof in detail will be omitted here.

FIG. 22(a) shows the tenth embodiment of the invention which is a modification of the first embodiment shown in FIGS. 1 to 3(c).

The holding member 31 has an extension 318 continuing straight from the outer wall thereof. The extension 318 is welded at a portion, as indicated at 318, to the inner wall of the air cover 121. Other arrangements are identical with those in the first embodiment, and explanation thereof in detail will be omitted here.

FIG. 22(b) shows a modification of the third embodiment shown in FIGS. 7(a) to 7(c).

The holding member 32 has an extension 329 continuing from the outer claw 322. The holding member 32 is forced into the gap between the insulation porcelain 2 and the inner wall of the air cover 121 in surface contact of the extension 329 with the inner wall of the air cover 121 and welded at a portion of the extension 329, as indicated at 328. Other arrangements are identical with those in the third embodiment, and explanation thereof in detail will be omitted here.

FIG. 23(a) shows a modification of the fourth embodiment as shown in FIGS. 9(a) and 9(b).

The holding member 33 has an extension 339 continuing straight from the outer wall thereof. The extension 339 is welded at a portion, as indicated at 338, to the inner wall of the air cover 121. Other arrangements are identical with those in the fourth embodiment, and explanation thereof in detail will be omitted here.

FIG. 23(b) shows a modification of the fifth embodiment shown in FIGS. 13(a) and 13(b).

The holding member 34 has an extension 349 continuing from the W-shaped elastic portion 342. The extension 349 is placed in surface contact with the inner wall of the air cover 121 and welded at a portion, as indicated at 348. Other arrangements are identical with those in the fifth embodiment, and explanation thereof in detail will be omitted here.

Figure 24A:
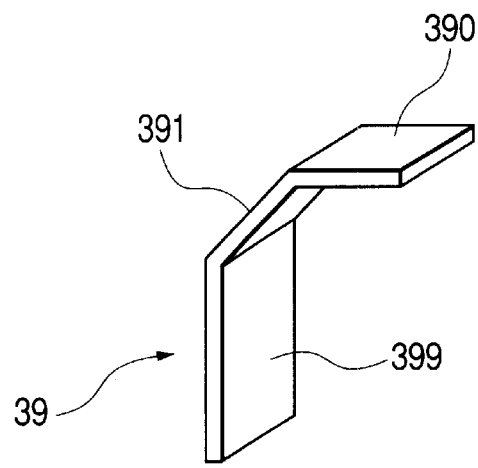
FIG. 24(a) is a perspective view which shows a holding member which is a modification of the one shown in FIG. 22(b)
Figure 24B:
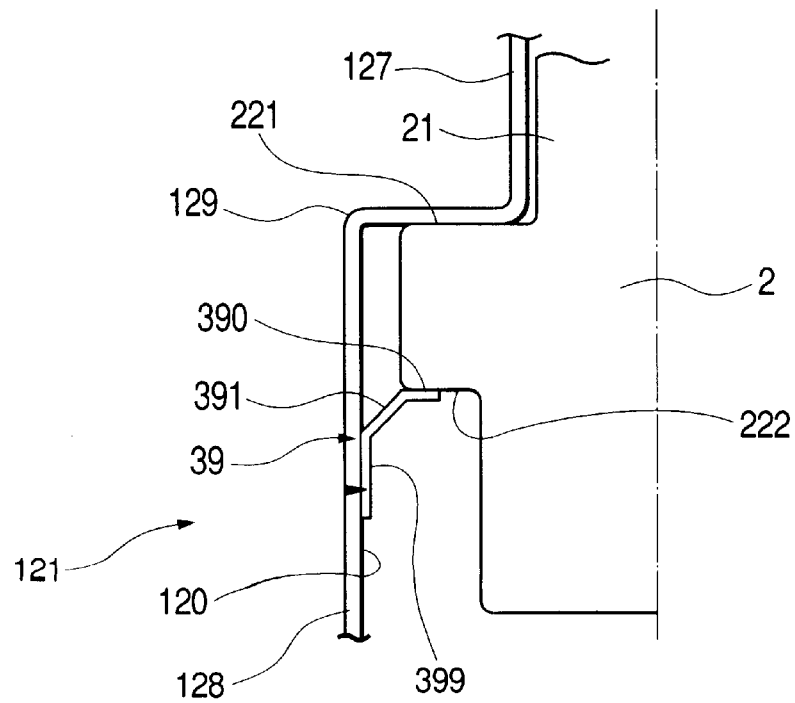
FIG. 24(b) is a partially vertical view which shows installation of an insulation porcelain within an air cover using the holding member of FIG. 24(a)

FIGS. 24(a) and 24(b) show the eleventh embodiment of the invention which is a modification of the one shown in FIG. 22(b).

Three holding members 39 (only one is shown for the sake of simplicity of illustration) are attached to the inner wall 120 of the air cover 121 to retain the insulation porcelain 2 firmly within the air cover 121.

Each of the holding members 39 is made of a spring plate consisting of a base 390, a mount portion 399, and a connecting portion 391 connecting between the base 390 and the mount portion 399. The mount portion 399 is attached in surface contact with the inner wall 120 of the air cover 121 and welded thereto to elastically urge the base 390 into constant engagement with the lower surface 222 of the flange 22, thereby retaining the insulation porcelain 2 firmly within the air cover 121.

Instead of the holding members 39, a one-piece annular spring having the same sectional shape as that of the holding members 39 may be used. This spring may be welded to the whole of a circumferential portion or discrete portions of the inner wall 120 of the air cover 121.

Other arrangements an effects of this embodiment are identical with those in the embodiment in FIG. 22(b), and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor measuring a given component content in a gas comprising:

a housing having a first end and a second end;

a sensing element disposed in said housing, said sensing element having a base portion and a gas-sensing portion, the base portion projecting from the first end of said housing, the gas-sensing portion projecting from the second end of said housing;

a first cover installed on the first end of said housing to cover the gas-sensing portion of said sensing element;

a plurality of electric terminals connected to said sensing element for establishing electric communication between said sensing element and an external device;

an insulator in which said electric terminals are disposed, said insulator including a body and a flange, the flange having a groove formed in a peripheral wall thereof;

a second cover installed on the second end of said housing to cover the base portion of said sensing element and retain said insulator therein, said second cover including a small-diameter portion, a large-diameter portion, and a shoulder connecting between the small-diameter portion and the large-diameter portion, the small-diameter portion being greater in diameter than the body of said insulator and smaller in diameter than the flange of said insulator, the large-diameter portion being greater in diameter than the flange of said insulator; and an elastic holding mechanism disposed between the groove of the flange of said insulator and an inner wall of the large-diameter portion of said second cover to be deformable elastically in a radius direction of said second cover to hold said insulator within said second cover firmly, wherein said elastic holding mechanism includes a plurality of springs disposed in the groove of the flange at regular intervals away from each other, wherein each of said springs is made of a corrugated plate which is disposed between the groove of the flange and the inner wall of the large-diameter portion of said second cover so as to urge the flange of said insulator elastically inwardly of said second cover, thereby holding said insulator within the second cover, wherein each corrugated plate has an extension wall which is placed in surface contact with the inner wall of said second cover and welded at a portion thereof to the inner wall of said second cover.

2. A gas sensor as set forth in claim 1, wherein said elastic holding mechanism is made of a spring ring disposed in the groove of the flange of said insulator.

3. A gas sensor as set forth in claim 2, wherein the spring ring has disposed on a periphery wall thereof a plurality of members which are so folded as to produce elastic pressure between the flange of said insulator and the inner wall of said second cover for holding said insulator within said second cover firmly.

4. A gas sensor measuring a given component content in a gas comprising:

a housing having a first end and a second end;

a sensing element disposed in said housing, said sensing element having a base portion and a gas-sensing portion, the base portion projecting from the first end of said housing, the gas-sensing portion projecting from the second end of said housing;

a first cover installed on the first end of said housing to cover the gas-sensing portion of said sensing element;

a plurality of electric terminals connected to said sensing element for establishing electric communication between said sensing element and an external device;

an insulator in which said electric terminals are disposed, said insulator including a body and a flange, the flange having a groove formed in a peripheral wall thereof;

a second cover installed on the second end of said housing to cover the base portion of said sensing element and retain said insulator therein, said second cover including a small-diameter portion, a large-diameter portion, and a shoulder connecting between the small-diameter portion and the large-diameter portion, the small-diameter portion being greater in diameter than the body of said insulator and smaller in diameter than the flange of said insulator, the large-diameter portion being greater in diameter than the flange of said insulator; and an elastic holding mechanism disposed between the groove of the flange of said insulator and an inner wall of the large-diameter portion of said second cover to be deformable elastically in a radius direction of said second cover to hold said insulator within said second cover firmly, wherein said elastic holding mechanism includes a plurality of springs disposed in the groove of the flange at regular intervals away from each other, wherein each of said springs is made of a corrugated plate which is disposed between the groove of the flange and the inner wall of the large-diameter portion of said second cover so as to urge the flange of said insulator elastically inwardly of said second cover, thereby holding said insulator within the second cover, and wherein each corrugated plate has an extension wall which is placed in surface contact with the inner wall of said second cover and welded at a portion thereof to the inner wall of said second cover.

5. A gas sensor as set forth in claim 4, wherein said elastic holding mechanism is made of a spring ring disposed in the groove of the flange of said insulator.

6. A gas sensor as set forth in claim 5, wherein the spring ring has disposed on a periphery wall thereof a plurality of members which are so folded as to produce elastic pressure between the flange of said insulator and the inner wall of said second cover for holding said insulator within said second cover firmly.

* * * * *